United States Patent [19]

Stoutamire

[11] Patent Number: 4,529,810
[45] Date of Patent: Jul. 16, 1985

[54] PREPARATION OF OPTICALLY-ACTIVE ALPHA-SUBSTITUTED CARBOXYLIC ESTERS AND ACIDS

[75] Inventor: Donald W. Stoutamire, Modesto, Calif.

[73] Assignee: Shell Oil Company, Houston, Tex.

[21] Appl. No.: 567,991

[22] Filed: Jan. 6, 1984

Related U.S. Application Data

[63] Continuation-in-part of Ser. No. 468,100, Feb. 22, 1983.

[51] Int. Cl.$^3$ .............................................. C07C 69/76
[52] U.S. Cl. ....................................... 560/105; 560/1; 560/9; 560/109; 560/152; 560/179; 560/205; 560/231; 562/496; 568/301
[58] Field of Search ...................... 560/105, 1, 9, 109, 560/179, 152, 205, 231; 568/301

[56] References Cited

FOREIGN PATENT DOCUMENTS 63731 11/1982 European Pat. Off. .

OTHER PUBLICATIONS

CA, 58:12479f, (1963).
*Organic Reactions,* 1946, pp. 124–127, R. Adams, editor; John Wiley & Sons, Inc., N.Y.
Pracejus, *Ann. Chem.,* 1960, 634, pp. 9–22.
Pracejus et al., *Ann. Chem.,* 1969, 722, pp. 1–11.
Jahme et al., *Tetrahedron Letters,* 1982, 23 (39), pp. 4011–4014.
Salz et al., *Tetrahedron Letters,* 1982, 23 (39), pp. 4017–4020.
Jahme et al., *Angew. Chem. Int. Ed. Engl.,* 1981, 20 (10), pp. 885–887.

*Primary Examiner*—Paul J. Killos

[57] ABSTRACT

Optically-active alpha-substituted carboxylic esters are prepared by treating a non-symmetrical ketene with an alcohol in the presence of an optically-active amine catalyst. Hydrolysis of the resulting esters, yields the optically-active acid corresponding to the non-symmetrical ketene.

26 Claims, No Drawings

PREPARATION OF OPTICALLY-ACTIVE ALPHA-SUBSTITUTED CARBOXYLIC ESTERS AND ACIDS

CROSS-REFERENCE TO RELATED APPLICATIONS

This application is a continuation-in-part of U.S. Ser. No. 468,100, filed Feb. 22, 1983.

BACKGROUND OF THE INVENTION

1. Field of the Invention

The present invention is directed to processes for the preparation of optically-active alpha-substituted esters and novel catalyst therefor.

2. Description of the Prior Art

Esters of alpha-disubstituted carboxylic acids are of interest because their stereoisomers usually have some different effects in biological systems. In the past, it usually had not been easy to prepare these optically-active alpha-chiral esters directly because the optically-active acids were not always readily accessible. Often, the optically-active acids were obtained by classical resolution, which was usually time consuming and not practical on a large scale.

The present process provides a process for preparing optically-active esters in high yield by a direct synthesis method, avoiding the cumbersome classical resolution of the optically-active acids.

SUMMARY OF THE INVENTION

The present invention is directed to a process for the preparation of an optically-active ester of an alpha-chiral (optically-active) carboxylic acid or a mixture enriched therein, which comprises treating a non-symmetrical ketene with an alcohol in the presence of an optically-active, nitrogen-base-substituted amino acid, a di- or polypeptide thereof or the reaction product of about one mole to about three moles of a ketene with one mole of the nitrogen-base-substituted amino acid or di- or polypeptide thereof as catalyst. The optically-active ester products include those of formula I below

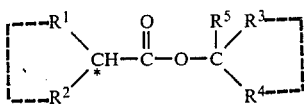

wherein $R^1$, $R^2$, $R^3$, $R^4$ and $R^5$ are substituents, * denotes the asymmetrically substituted carbon atom, and the broken lines are optional bonds. Depending on the reactants selected, the product ester of the process of the invention is enriched in one of its optically-active stereoisomers or enriched in one enantiomer pair, the enrichment being over an equimolar amount of stereoisomer(s) expected from the reaction of an equimolar amount of a non-symmetrical ketene with an achiral or chiral (racemic or optically-active) alcohol.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Tetrahydrofuran and dioxane are also useful. Preferably, the reaction is conducted in the presence of toluene.

Any non-symmetrical ketene is useful (provided it does not contain substituent groups which form other stable reaction products with the alcohol). The non-symmetrical ketene has the formula II

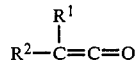

wherein $R^1$ and $R^2$ each independently is a different alkyl, aralkyl, alkoxy, aryloxy, alkylthio, alkylsulfonyl, arylthio or arylsulfonyl group containing from 1 to 10 carbon atoms or a cycloalkyl group containing 3 to 7 ring carbon atoms, or $R^2$ is also an alkenyl or alkynyl group containing 2 to 10 carbon atoms; a naphthyl group, a phenyl group, a heterocyclic group containing 5 or 6 ring atoms, one of which is oxygen, sulfur or nitrogen, and the remainder are carbon atoms; or is an amino group disubstituted by acyl or alkyl containing up to 10 carbon atoms or a phenyl group; or $R^1$ and $R^2$, when taken together with the carbon atom to which they are attached, form a non-symmetrical cycloalkyl group containing 4 to 7 ring carbon atoms and 4 to 14 carbon atoms. The $R^1$ and $R^2$ groups can be optionally substituted by one or more of halogen atoms having an atomic number of from 9 to 35, alkyl or haloalkyl containing 1 to 4 carbon atoms, alkenyl or haloalkenyl containing 2 to 4 carbon atoms, haloalkoxy or alkoxy of 1 to 4 carbon atoms, haloalkylthio or alkylthio of 1 to 4 carbon atoms or equivalent kinds and sizes of substituents which may contain the same or greater carbon number.

One embodiment of non-symmetrical ketenes used in the process of the invention is that which is used in pyrethroid esters, including those esters having an acid moiety described in U.S. Pat. Nos. 4,062,968 and 4,199,595. Examples of such ketenes include those having the formula II in which $R^1$ is isopropyl or cyclopropyl optionally substituted by one or more chlorine atoms and $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy or haloalkoxy in which the halogens are bromine, chlorine or fluorine, and the alkyl groups contain 1 or 4 carbon atoms.

Of particular interest as non-symmetrical ketene reactants, because their resulting acids can be used to make esters of high pesticidal activity, are those ketenes having the formula II in which $R^1$ is isopropyl and $R^2$ is a phenyl group para-substituted by halogen, alkyl, haloalkoxy in which the halogen, e.g. chlorine or fluorine and the alkyl contain 1 to 4 carbon atoms, e.g. methyl. For example, the ketene is (4-chlorophenyl)isopropylketene, (4-(difluoromethoxy)phenyl)isopropylketene or (4-(trifluoromethyl)-3-chlorophenyl)-(benzyloxycarbonyl)amino)isopropylketene, and the like.

Any chiral or achiral alcohol is useful in the process (provided it does not contain substituent groups which form other stable reaction products with the non-symmetrical ketene or the catalyst). Preferably, the alcohol is a symmetrical or non-symmetrical (racemic or optically-active) alcohol of formula III

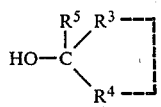

wherein $R^3$ is a hydrogen atom or an optionally substituted hydrocarbyl or heterocyclic group; $R^4$ is a hydrogen atom, an optionally substituted hydrocarbyl group; or $R^3$ and $R^4$, when taken together with the carbon atom to which they are attached, form an alkylene group (saturated, unsaturated) as denoted by the dotted line; and $R^5$ is a hydrogen atom, an optionally substituted hydrocarbyl group, or a group $—C(=X^1)X^1R^6$ in which each $X^1$ is independently O or S and $R^6$ is an optionally substituted hydrocarbyl group. Preferably, the optional substituents are halogen atoms having an atomic number of from 9 to 35, inclusive.

The hydrocarbyl groups represented by $R^3$, $R^4$, $R^5$ and $R^6$ in the formula III may be, for example, an alkyl, a cycloalkyl, alkenyl, alkynyl, aralkyl or an aryl group of up to 20 carbon atoms, preferably up to 10 carbon atoms, or $R^3$ in the formula III may be a carbocyclic or an O or S heterocyclic aryl group. Examples of carbocyclic aryl groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2 (1963), page 702: obtained by replacement of one or more carbon atoms of a carbocyclic aromatic compound by a heteroatom selected from O or S, and also include those heterocyclic compounds having five-membered rings which show aromatic characteristics and are mentioned on page 703 of said volume. Optional substituents include one or more of halogen atoms having an atomic number of from 9 to 35, inclusive, or an alkyl, alkenyl or alkoxy group containing 1 to 6 carbon atoms, each optionally substituted by one or more halogen atoms, optionally substituted phenoxy, phenyl, benzyl or benzoyl and equivalent kinds of substituents. Non-limiting examples of the alcohol reactant include methanol, isopropanol, cyclohexanol, cyclohexylmethanol, 3-phenoxybenzyl alcohol, alpha-ethynyl-3-phenoxybenzyl alcohol, 3-phenoxy-4-fluorobenzyl alcohol, 3-phenylbenzyl alcohol, 2,6-dimethyl-3-phenylbenzyl alcohol, alpha-ethynyl-3-phenoxy-4-fluorobenzyl alcohol, 5-benzyl-3-furylmethanol and the like.

Preferably, the alcohol is an optically-active aromatic alcohol having the desired alpha substitution and includes those alcohols having as $R^3$ any of a variety of optionally substituted rings having aromatic character, for example, a phenyl, naphthyl, 2-furanyl, phenoxyalkyl, and the like optionally ring substituted by one or more of alkyl, alkenyl or alkynyl of up to 4 carbon atoms, halogen selected from chlorine, bromine or fluorine, benzyl, benzoyl, furanyl, phenoxy or phenthio and the like; $R^4$ is a hydrogen atom; and $R^5$ (the alpha substituent) is an optionally substituted alkyl, cycloalkyl, alkenyl, alkynyl, aralkyl or aryl group containing up to 8 carbon atoms, or $—C(=X^1)X^1R^6$ in which each $X^1$ is independently O or S and $R^6$ is an alkyl, alkenyl, aralkyl or aryl group containing up to 10 carbon atoms. Preferably, the $R^3$ is an optionally substituted aromatic ring selected from phenyl, naphthyl or 2-furanyl, $R^4$ is a hydrogen atom and $R^5$ is an alkyl, cycloalkyl, alkenyl, alkynyl, aralkyl or aryl group containing up to 8 carbon atoms. Optional substituents on $R^3$ are preferably halogen and/or benzyl, phenyl, phenoxy or phenthio, and the like. Non-limiting examples of the optically-active alcohol include alpha-(trifluoromethyl)3-benzylbenzyl alcohol, alpha-methyl-5-benzyl-3-furylmethyl alcohol, alpha-carbmethoxy-3-(phenyl)benzyl alcohol, alpha-allenyl-4-fluoro-3-phenoxybenzyl alcohol, alpha-(phenylethynyl)-3-phenoxy-4-fluorobenzyl alcohol, alpha-(1,2-dibromovinyl)-3-(phenylthio)benzyl alcohol, alpha-methylbenzyl alcohol, alpha-cyclopropylbenzyl alcohol, alpha-ethynyl-3-phenoxybenzyl alcohol and the like.

In one embodiment, the alcohol has the formula

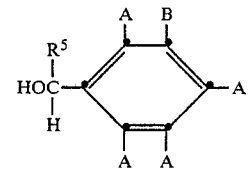

wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive, or is a group

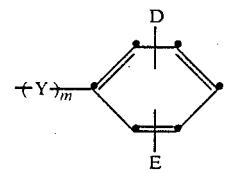

in which Y is O, $CH_2$, or $C(O)$; m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; and $R^5$ is a hydrogen atom or an alkyl, alkenyl, alkynyl, aralkyl or aryl group containing up to 8 carbon atoms. When $R^5$ is other than a hydrogen atom, the alcohol is used in the racemic, or preferably, in the optically-active form.

The optically-active, nitrogen-base-substituted amino acid catalyst comprises a substituted amino acid which is preferably any acyclic, carbocyclic, aromatic or heterocyclic amino acid containing up to 20 carbon atoms, preferably up to 10 carbon atoms, additionally substituted by a moderate to weakly basic nitrogen-base-substituent or is the reaction product thereof with about one to about three moles of a ketene. Suitable nitrogen-base substituents include optionally substituted nitrogen heterocyclic groups or amino groups, each optionally substituted by alkyl or cycloalkyl groups containing 1 to 6 carbon atoms or by optionally substituted phenyls. Other optional substituents include hydroxy, alkyl, alkoxy, amino, alkylthio, amido and the like. Examples of nitrogen-heterocyclic groups include thiazolyl, imidazolyl, pyrrolyl, benzopyrrolyl and the like.

In one embodiment of the invention, the catalyst is an optically-active histidine-containing peptide catalyst comprising a histidine or a histidine-containing di- or polypeptide in which at least one of the histidinyl free N-H and free COOH groups is modified with a protecting group into the form of an amide (or acid addition salt thereof) and an ester group respectively; or the reaction product of one mole of a histidine or a histidine-containing mono-, di- or polypeptide with from about one mole to about three moles of a ketene per mole of histidine group.

The di- or polypeptide is linear or cyclic. These peptides usually contain from about 2 up to about 16 peptide units, preferably 2 to 4 peptide units. Nitrogen-substituted amino acids, including these histidine-containing di- and polypeptides, are prepared by conventional peptide synthesis, for example, as in Greenstein, J. P. and M. Winitz, "Chemistry of the Amino Acids", John Wiley & Sons, Inc., New York, 1961.

The peptides of the histidine-containing catalyst are preferred, especially in the cyclic dipeptide form. The di- or polypeptides may also contain alanine, and those prepared with alanine, phenylalanine or alanine derivatives, are preferred.

In one embodiment of the invention, the asymmetric carbon atoms in the histidine-containing peptide catalyst has the D configuration. Choice of chirality of the catalyst can be made so as to provide the chirality desired in the product.

Functional groups in the amino acid catalyst can contain protecting groups; any conventional amino acid protecting group known in the art can be used. For example, the protecting group is an organic acid in the case of the free N-H or an alcohol in the case of the free COOH. Any organic acid and alcohol which will not interfere with the reaction can be used as the protecting group. Preferably, the protecting group is an other amino acid. Any amino acid can be used, but, preferably, the amino acid is non-heterocyclic and is a monoamino or diamino-alkanoic or aralkanoic acid, such as alanine, phenylalanine, glutamic acid, glycine and the like.

The acid addition salts of the catalysts are formed with any acid that will not interfere with the reaction. Suitable inorganic acids include hydrohalogenic acids, such as hydrochloric or hydrobromic; sulfur acids, such as sulfuric or toluenesulfonic; and phosphorus acids, such as phosphoric or phenylphosphonic; and organic acids, such as oxalic acid and the like, are also suitable to form the salts.

When preparing the di- or polypeptide catalyst also having an alanine (containing moiety), it is prepared from alanine or its derivatives; this includes alanine, beta-alanine, phenylalanine, 3,4-dihydroxyphenylalanine and the like. When preparing the catalyst from a histidine (containing moiety including substituted histidines), it is preferably histidine, 3-methylhistidine, 3-ethylhistidine, 3-propylhistidine, 3-benzylhistidine, 1-methylhistidine, 1-ethylhistidine, 1-propylhistidine, or 1-benzylhistidine, and the like. In one embodiment of the invention, 1-methylhistidine or a 3 methylhistidine is the moiety. Preferably, the catalyst is a cyclic dipeptide containing a histidine moiety and an alanine moiety.

The adducts (reaction products) with a ketene are prepared to contain from about one mole to about three moles of a ketene per mole of nitrogen-based amino acid unit, and preferably about one mole of ketene with a (cyclic) dipeptide. Obviously, it is preferable to form the adduct in situ with the non symmetrical ketene reactant of the process, which is described below under process conditions. However, treatment of the optically-active catalyst with about 1.1 to 5 moles of a ketene, preferably in the absence of a solvent or any solvent used in preparing the ketene, is suitable. The ketene may also be a similar kind but symmetrical ketene, e.g. dimethylketene, diphenylketene or ketene itself.

Non-limiting examples of the optically-active histidine-containing catalyst include histidine, alpha-methyl-histidine, 1-methylhistidine, 3-methylhistidine, cyclo(histidyl-histidine), (benzyloxycarbonylalanyl)histidine methyl ester, cyclo(alanyl-histidine), cyclo(phenylalanyl-histidine), histidine methyl ester hydrochloride, cyclo(beta-phenylalanyl-1-methylhistidine), cyclo(beta-phenylalanyl-3 methylhistidine), histidine ethyl ester dihydrochloride, anserine, cyclo(valyl-histidine), glycyl-histidine, cyclo(phenylalanyl-glycyl-histidine), cyclo(leucyl-histidine), cyclo(homophenylalanyl-histidine), cyclo(phenylalanyl-methylhistidine), N-alpha-(beta-naphthoyl)histidine, histidylalanine, histidyl-phenylalanamide hydrochloride, histidyl-phenylalanine, cyclo(histidyl-proline), cyclo(glycyl-histidine) in free or protected form or a reaction product of these materials with a ketene. Also, cyclo(phenylalanyl-histidine) adduct with (4-(difluoromethoxy)phenyl)isopropylketene, histidine adduct with ketene, cyclo(glycyl-histidine) adduct with (4-(difluoromethoxy)phenyl)isopropylketene, and histidylalanine adduct with dimethylketene and the like.

In one embodiment of the invention, the catalyst has the formula

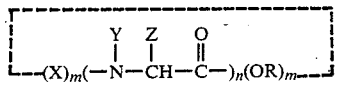

wherein X is H, alkyl or

each R is independently alkyl or cycloalkyl of up to 7 carbon atoms, optionally substituted phenyl, benzyl or the like; each of the n units of

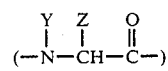

is independently substituted in which Y is hydrogen, acyl, alkyl, or aralkyl of up to 10 carbon atoms; Z is the residue of common amino acids that do not interfere in the process of the invention including benzyl, 3-carboxypropyl, 3-aminopropyl, mercaptomethyl, 4-hydroxybenzyl, imidazol-4-ylmethyl; each m is 0 or 1, n is 1 to 16, when each m is 0, the catalyst has a cyclic structure denoted by the dotted line; with the proviso that at least one histidine or substituted histidine unit is included in the catalyst; or the reaction products of the above catalysts with from about one to about three moles of a ketene.

The amount of catalyst can vary. For example, it can be used in the range of from about 0.01 to about 5 mole percent based upon the weight of the alpha-substituted alcohol present, preferably about 0.1 to about 2.5 mole percent.

When the catalysts are prepared by conventional methods in the presence of water, they can, if solid, also contain water of crystallization. The optically-active, nitrogen-based amino acid, e.g., histidine-containing peptide, catalyst of the invention, thus, includes the presence or absence of water of crystallization when solid.

The reaction is conducted by adding the non-symmetrical ketene to the alcohol, which may be dissolved in a solvent, in the presence of an optically-active catalyst, agitating the mixture, e.g., by stirring, and maintaining the reaction conditions for an amount of time to effect the formation of the optically-active ester. Separation and recovery of the optically-active ester product are achieved by conventional techniques, including extraction and the like.

The molar ratio of the starting materials, non-symmetrical ketene and alcohol can vary. For example, the molar ratio of ketene to alpha-substituted alcohol is suitably from about 10:1 to about 1:10 and, preferably, from about 5:1 to about 1:5. However, it is desirable to have a molar excess of ketene to alpha-substituted alcohol of from about 1:1.1 to about 1:1.5.

The temperature of the reaction as well as the pressure can vary. At normal pressures, the temperature is from about 10° C. to about 50° C., more or less. Ambient temperatures of about 15° C. to about 35° C. are convenient.

The alcohols are generally known in the literature, for example, U.S. Pat. Nos. 3,927,068, 4,219,564, 4,238,504, 4,322,432, 4,166,064, 4,045,575, 4,175,134, European Pat. No. 50,093 and the like. They can be either directly synthesized or for optically-active forms resolved by methods conventionally known in the art for asymmetric alcohols.

Another aspect of the present invention is directed to a process for the preparation of an optically-active carboxylic acid which comprises reacting a non-symmetrical ketene with an optically-active or achiral alcohol in the presence of an optically-active, nitrogen-base-substituted amino acid, a di- or polypeptide thereof or the reaction product of about one to about three moles of a ketene with one mole of nitrogen-base-substituted amino acid, or di- or polypeptide thereof, followed by separation of the ester diastereoisomers and hydrolysis of the resulting ester diastereoisomer to yield the optically-active carboxylic acid corresponding to the non-symmetrical ketene.

The process conditions for formation of the ester are the same as described above as are the non-symmetrical ketene, alcohol, the catalyst and the like. It is desirable, however, that the non-symmetrical ketene and the optically-active alcohol be of dissimilar molecular weights so that upon hydrolysis the desired optically-active carboxylic acid can be separated and recovered by conventional techniques, such as distillation, extraction, crystallization, and the like.

Again, any pair of diastereomers formed from the non-symmetrical ketene reaction with the optically-active alcohol are separated by conventional techniques used for separating diastereoisomers, e.g. chromatographic separation and the like.

The hydrolysis is conducted in the presence of water or source of water and under acidic or basic conditions conventional for hydrolysis of esters. Conveniently, the hydrolysis is conducted at ambient temperature with an aqueous acid, such as mineral acids, including hydrochloric and the like. If a solvent is used in the hydrolysis, it is conveniently any used in the steps of forming the ester.

The non-symmetrical ketenes are generally known in the art or are novel. Ketenes used in the present invention can be prepared by treating the corresponding acid halide with a tertiary amine.

The tertiary amine can be any alkyl, aryl or heterocyclic nitrogen base including mono- or polyamines and the like. Preferably, the tertiary amine is an amine in which any alkyl groups contain from 1 to 10 carbon atoms, any aryl or aralkyl groups contain from 6 to 20 carbon atoms and 1 to 2 hydrocarbyl rings, and any heterocyclic amines contain at least one ring nitrogen atom in a 5 or 6 membered heterocyclic ring optionally containing a sulfur or oxygen atom or another nitrogen atom such as trimethylamine, triethylamine, tri-n-propylamine, pyridine and the like. The tertiary amine desirably contains three alkyl groups of 1 to 4 carbon atoms, for example: trimethylamine, tri-n-propylamine, and especially triethylamine or trimethylamine.

The reaction is conducted in the presence or absence of a solvent. When a solvent is used the solvent is preferably a non-hydroxylic solvent such as hydrocarbons, chlorinated hydrocarbons, ethers and the like. For example, suitable solvents are alkanes containing from 5 to 10 carbon atoms such as n-pentane, n-hexane, n-heptane, n-octane, n-nonane, n-decane and their isomers. Petroleum fractions rich in alkanes are also suitable, for example, gasoline with a boiling range at atmospheric pressure of between 40° and 65° C., between 60° and 80° C. or between 80° and 110° C. Petroleum ether is also suitable. Cyclohexane and methylcyclohexanes are examples of useful cycloalkanes containing from 6 to 8 carbon atoms. Aromatic hydrocarbon solvents can contain from 6 to 10 carbon atoms, for example, benzene, toluene, o-, m- and p-xylene, the trimethylbenzenes, p-ethyltoluene and the like. Suitable chlorinated hydrocarbons contain from 1 to 4 chlorine atoms in combination with an alkane chain containing from 1 to 4 carbon atoms or with a benzene ring, for example, carbon tetrachloride, chloroform, dichloromethane, 1,2-dichloroethane, trichloroethane, perchloroethane, chlorobenzene and 1,2- or 1,3-dichlorobenzene and the like. Ethers are generally those containing from 4 to 6 carbon atoms such as diethyl ether, methyl tert-butyl ether and diisopropyl ether and the like. Tetrahydrofuran and dioxane are also useful.

In the preparation of the non-symmetrical ketene, the molar ratio of the starting materials can be varied widely. For example, the molar ratio of acid halide to base is from about 10:1 to about 1:10, and preferably from about 5:1 to about 1:5. However, it is desirable to have a molar excess of base to acid halide. Therefore, a molar ratio of acid halide to base is desirably from about 1:1 to about 1:5 and conveniently from about 1:1.2 to about 1:2.

In the preparation of the non-symmetrical ketene, the temperature can be varied widely. At normal pressure, for example, the temperature of reaction can be varied but is preferably, for example, from about 10° C. to 40° C. more or less, although higher temperatures of up to about 75° C. to about 95° C. have also been found useful.

Separation and recovery of the product non-symmetrical ketene are achieved by conventional methods, including crystallization and the like.

The process of the invention is useful for preparing non-symmetrical ketenes from any acid halides which do not contain substituted groups which would react with the base. For example, the acid halide can be that of an acyclic, alicyclic, aromatic or heteroaromatic acid. Preferably, the acid halide has the formula IV

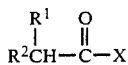

wherein X is the halogen atom, such as chlorine or bromine, $R^1$ and $R^2$ each independently is an alkyl, aralkyl, alkoxy, aryloxy, alkylthio, alkylsulfonyl, arylthio, or arylsulfonyl group containing from 1 to 10 carbon atoms or a cycloalkyl group containing 3 to 7 ring carbon atoms, or $R^1$ and $R^2$, when taken together with the carbon atom to which they are attached, form a non-symmetrical cycloalkyl group containing 4 to 7 ring carbon atoms; $R^2$ is also an alkenyl or alkynyl containing from 2 to 10 carbon atoms, a naphthyl group, a phenyl group, a heterocyclic group containing 5 or 6 ring atoms, one of which is oxygen, sulfur or nitrogen, and the remainder are carbon atoms or is an amino group disubstituted by acyl or alkyl containing up to 10 carbon atoms or a phenyl group. The $R^1$ and $R^2$ groups can be optionally substituted by one or more of halogen of atomic numbers 9 to 35, an alkyl, haloalkyl or cycloalkyl group containing up to 7 carbon atoms, alkenyl or haloalkenyl group of 2 to 4 carbon atoms, haloalkoxy or alkoxy group of 1 to 4 carbon atoms, haloalkylthio or alkylthio group of 1 to 4 carbon atoms or equivalent kinds of substituents.

One embodiment of acid halides are halides of pyrethroid acids, including those of U.S. Pat. Nos. 4,062,968 and 4,199,595. Examples of such acid halides include those having the formula IV in which $R^1$ is isopropyl or cyclopropyl, optionally substituted by one or more chlorine atoms and $R^2$ is an alkyl group containing 1 to 6 carbon atoms; an alkenyl group containing 2 to 6 carbon atoms; a naphthyl group, a phenyl group or a (benzyloxycarbonyl)phenylamino group, each optionally ring-substituted by one or more of halogen, alkyl, haloalkyl, alkoxy or haloalkoxy in which the halogens are bromine, chlorine or fluorine and the alkyl groups contain 1 or 4 carbon atoms. For example, the acid halide is isopropyl-(4-chlorophenyl)acetyl chloride, isopropyl(4-(difluoromethoxy)phenyl)acetyl chloride or isopropyl-(4-(trifluoromethyl-3-chlorophenyl)benzyloxycarbonylamino)acetyl chloride and the like.

Preferably, in formula IV, $R^1$ is isopropyl and $R^2$ is a phenyl group optionally substituted by halogen, an alkyl or haloalkyl group of 1 to 4 carbon atoms or an alkoxy or haloalkoxy group containing 1 to 4 carbon atoms, preferably at the para position, especially useful are 4-chlorophenyl, 4-(difluoromethoxy)phenyl, 4-methylphenyl, 4-tert-butylphenyl and the like. Many of the ketenes of the invention are known in the art per se, for example, (4-chlorophenyl)isopropylketene, as in U.S. Pat. No. 4,199,527. Some other non-symmetrical ketenes are believed to be novel, for example, including (4-(difluoromethoxy)phenyl)isopropylketene.

The ester products are of use per se, e.g. as pesticides, pharmaceuticals and the like or are intermediates to the corresponding optically-active acids obtained by hydrolysis thereof using conventional hydrolysis procedures. The acids are useful, per se, or as intermediates to esters and the like in pharmaceuticals, pesticides, herbicides, etc.

Illustrative Embodiments

The following embodiments are provided for the purpose of illustrating the invention and should not be regarded as limiting it in any way. The identity of the products was confirmed by infrared and nuclear magnetic resonance spectral analyses as necessary.

EMBODIMENT 1—N-(BENZYLOXYCARBONYL)-D-PHENYLALANINE

A 15.0 g sample of D-phenylalanine was dissolved in 45 ml of aqueous solution containing 7.26 g of 50% sodium hydroxide. This solution was stirred at 0°–10° C. as 16.3 g of benzyl chloroformate was added rapidly in portions. The resulting reaction was mildly exothermic, and shortly after addition, solids precipitated. An additional 45 ml of water and 3.63 g of 50% sodium hydroxide were added, causing most of the solids to redissolve. The reaction mixture was stirred for 20 minutes and then acidified with 6 N hydrochloric acid. The resulting solids were filtered, washed with water and then with hexane, and dried by suction and then under vacuum to give 47 g of white solids. These solids dissolved in ether were washed twice with 1 N hydrochloric acid and then with water, dried over $MgSO_4$ and stripped to 35° C. at 2.5 mm Hg to give 27.7 g of the desired product as a colorless oil.

EMBODIMENT 2—N-(BENZYLOXYCARBONYL)-D-PHENYLALANINE, P-NITROPHENYL ESTER

A 300 ml three-neck flask with stirrer and dropping funnel was charged under a nitrogen atmosphere with 27 g of the acid of Embodiment 1 above in 135 ml of pyridine, followed by 13.2 g of p-nitrophenol. The resulting solution was cooled to 0° to 10° C. as 14.6 g of phosphorus oxychloride was added. The resulting mixture was warmed to 25° C., stirred for 15 minutes, then poured into 300 ml of ice water. Filtration of the resulting solid, followed by washing with water and drying by suction, gave 33 g of product. This was crystallized from 340 ml of hot ethyl alcohol with chilling to −5° C. The product was filtered, washed with chilled ethyl alcohol, then with hexane, and sucked dry to give 28.7 g of the desired product, m.p. 122.5°–124.5° C., $[\alpha]_D^{23}$ +24.7(c 2.0, dimethylformamide).

EMBODIMENT 3—N-BENZYLOXYCARBONYL-D-PHENYLALANYL-D-HISTIDINE METHYL ESTER

To a stirred solution of 5.0 g of D-histidine methyl ester hydrochloride in 40 ml of methylene chloride was added 4.18 g of triethylamine followed by 8.27 g of the nitrophenyl ester prepared as in Embodiment 2 above. The reaction mixture immediately became bright yellow and solids began to precipitate. The reaction mixture was stirred for 2 hours, then stored overnight at −10° C. The reaction mixture was rewarmed to room temperature, and 0.6 ml of triethylamine was added. Then, 490 mg of the D-histidine methyl ester hydrochloride was added, and stirring was continued for 2 hours. The reaction mixture was washed with 20 ml of water, then twice with 20 ml of 10% ammonium hydroxide, and then twice with 20 ml of water. All the washes were back-extracted serially with 20 ml of methylene chloride, and the combined organic phases were dried with MgSO$_4$ and stripped to 100 ml, filtered through silica, followed by 25 ml of 20% methanol in ethyl acetate. The resulting eluate was stripped to 40 ml and diluted to 120 ml with diethyl ether; the precipitated solid was filtered, washed with diethyl ether, and dried by suction to give 5.66 g of the desired product as a white solid, m.p. 114.5°–117° C. $[\alpha]_D^{20}$ −55.5(c 2 in CHCl$_3$).

EMBODIMENT 4—CYCLO(D-PHENYLALANYL-D-HISTIDINE)

5.60 g of methyl ester of Embodiment 3 above was stirred and hydrogenated in 100 ml of methanol over 220 mg of 10% palladium on carbon at atmospheric pressure. After 3 hours, solids began to precipitate; an additional 25 ml of methanol was added to facilitate stirring. After 7 hours, an additional 280 ml of methanol was added as the mixture was heated to reflux. The mixture was filtered hot, and the filtrate was stripped to a gel-mush and mixed with 100 ml of diethyl ether. The resulting solid was filtered, washed with diethyl ether, and dried by suction and then under high vacuum at 35° C. to give 3.29 g of the desired product as an off-white powder, $[\alpha]_D^{23}$ = +68.5(c 2. 0 in CH$_3$COOH).

EMBODIMENT 5—(4-CHLOROPHENYL)ISOPROPYLKETENE

To a solution of 2.31 g of isopropyl(4-chlorophenyl)acetyl chloride in 10 ml of methylene chloride was added in one portion 1.5 g of triethylamine. After 18 hours, 15 ml of heptane was added to the mixture and the triethylamine hydrochloride was removed by filtration. The filtrate was stripped and 10 ml of heptane was added and the resulting mixture was filtered and stripped to give a yellow residue, which was dissolved in 5 ml heptane for GLC analysis. The resulting solution was distilled through a Bantam-ware short-neck head from an oil bath at 125°–150° C. and head temperature of 110°–100° C. at 0.2–0.05 mm to give 0.95 g of distillate and 0.81 g of gum. The distillate was crystallized twice from 2 volumes of hexane at −80° C. The solid was melted and stripped to about 40° C. at 0.5 mm to give 0.42 g of the desired product as a yellow liquid.

EMBODIMENT 6—(4-CHLOROPHENYL)ISOPROPYLKETENE

A sample of 53.2 g of isopropyl(4-chlorophenyl)acetic acid was treated with 21.5 ml of thionyl chloride in a 500 ml flask and heated slowly to 80° C. and maintained at 80° C. for 20 minutes. The reaction mixture was allowed to stand at room temperature for 2 days. The volatiles were stripped to 75° C. at 0.5 mm Hg. The resulting yellow liquid was diluted with 250 ml of methylene chloride followed by addition of 38.0 g of triethylamine. The mixture was stirred until triethylamine hydrochloride began to precipitate after 30 minutes. After 16 hours, the reaction mixture was filtered and solid triethylamine hydrochloride was washed free with heptane. Most of the solvent was stripped from the filtrate by rotary evaporation at 50° C. The residue was diluted with 75 ml of heptane and additional triethylamine hydrochloride was removed by filtration as above. The filtrate was restripped and rediluted with 75 ml heptane and refiltered with the aid of 25 ml of heptane. The filtrate was cooled in dry ice, seeded and crystallized. The resulting crystals were filtered with a filter stick and washed with chilled heptane. The filtered solids were melted, diluted with one-half volume heptane, crystallized at −80° C. and the collected solid was melted and stored at −80° C. The filtrate solution was warmed, stripped of most solvent, then distilled through a Bantam ware short path head at 0.05 to 0.06 mm Hg from an oil bath at 90°–120° C. Total distillate was 14.5 g collected as a bright yellow-orange liquid at a head temperature of 60°–85° C. The distillate was crystallized from an equal volume of pentane at −80° C., filtered and washed twice with heptane as above to give, on warming, a second melt. The stripped filtrates totalling 5.79 g were crystallized as above in a 6-inch test tube and the melt was recrystallized immediately as described above to give a third melt. The three melts were combined and stripped to 50° C. at 5 mm Hg to give 29.4 g of the desired ketene as a yellow liquid.

EMBODIMENT 7—(4-CHLOROPHENYL)ISOPROPYLKETENE

To 57.75 g of isopropyl(4-chlorophenyl)acetyl chloride was added 69.4 ml of triethylamine. The mixture was allowed to stand overnight at 20° C. The resulting mushy solid was crushed, diluted with 300 ml of redistilled hexane and filtered. The solids were washed three times with 75 ml of hexane, filtered and dried by suction with calcium chloride dried air to give 32 g triethylamine hydrochloride. The combined hexane solutions of ketene slowly deposited additional solids; the mixture was let stand at room temperature overnight with the flask wrapped in aluminum foil, and was filtered again to give 0.75 g of additional solids. The solvent was removed from the filtrate by rotary evaporation, then taken briefly to 1 mm Hg. To the mixture was added 500 ml of hexane, and after filtration, the filtrate was stripped to a yellow oil. This oil was distilled through a Bantam-ware short path head at 0.5 mm Hg to give 28.61 g of the desired ketene as a yellow liquid, d$^{20}$ 1.10.

EMBODIMENT 8—(4-DIFLUOROMETHOXY)PHENYL)ISOPROPYLKETENE

Following procedures similar to those described in Embodiment 7 above, the desired product is prepared by treating isopropyl(p-(difluoromethoxy)phenyl)acetyl chloride with triethylamine.

EMBODIMENT 9—ALPHA-METHYLBENZYL ALPHA-ISOPROPYL-4-CHLOROPHENYLACETATE

To a 1 dram vial fitted with a septum cap and magnetic stirrer was added 4 mg of cyclo-(L-phenylalanyl-L-histidine) followed by 0.5 ml of toluene, 0.122 ml of alpha-methylbenzyl alcohol, 0.18 ml of the (4-chlorophenyl)isopropylketene. The reaction mixture was stirred at ambient temperature, warmed for an hour and then left overnight. The product was washed with a small amount of dilute 1 N hydrochloric acid, then with water, dried (MgSO4), filtered and diluted with 1 ml of toluene for analysis. The product ester had a diastereoisomer ratio of 41/59 by GLC column analysis, and an optical rotation of −1.26° (1 dm cell).

EMBODIMENT 10—ISOPROPYL-(4-CHLOROPHENYL)ACETIC ACID ESTERS

Following procedures similar to those described in Embodiment 9, (4-chlorophenyl)isopropylketene is treated with one of the following alcohols: alpha-methylphenethyl, alpha-isopropylbenzyl, alpha-ethylbenzyl, alpha-methyl-p-chlorobenzyl, alpha-methyl-p-(methoxy)benzyl, alpha-methyl-1-naphthylmethyl, ethyl lactate, alpha-n-propylbenzyl, alpha-ethyl-1-naphthylmethyl, alpha-ethyl-2-naphthylmethyl, and alpha-methyl-2-naphthylmethyl.

The ester diastereoisomers are separated by chromatographic separation to give the ester enriched in one form of the optically-active isopropyl-(4-chlorophenyl)acetic acid.

EMBODIMENT 15—METHYL ALPHA-ISOPROPYL-4-CHLOROPHENYLACETATE AND ISOPROPYL-(4-CHLOROPHENYL)ACETIC ACID

To a 1 dram vial having a magnetic stirrer and septum cover and charged with 4 mg of cyclo(D-phenylalanyl-D-histidine) is added by syringe 0.5 ml toluene, 0.122 ml of optically-active alpha-methylbenzyl alcohol, 0.0445 ml methanol and 0.18 ml (4-chlorophenyl)isopropylketene. The reaction mixture is stirred at ambient temperature overnight. The resulting mixture is washed with a small amount of dilute 1 N hydrochloric acid, then with water, dried (MgSO4), filtered to obtain the enriched ester product.

The product ester is hydrolyzed to give the corresponding optically-active isopropyl-(4-chlorophenyl)acetic acid.

What is claimed is:

1. A process for the preparation of an optically-active ester of an alpha-chiral (optically-active) carboxylic acid or a mixture enriched therein, which comprises treating a non-symmetrical ketene with an alcohol in the presence of an optically-active, nitrogen-base-substituted amino acid, a di- or polypeptide thereof or the reaction product of about one mole to about three moles of a ketene with one mole of the nitrogen-base-substituted amino acid or di- or polypeptide thereof as catalyst.

2. A process according to claim 1 wherein the nitrogen-base-substituent is an optionally-substituted nitrogen-heterocyclic group or an optionally-substituted amino group.

3. A process according to claim 2 conducted in the presence of an optically-active histidine-containing peptide catalyst.

4. A process according to claim 1 wherein the non-symmetrical ketene is treated with an alcohol having the formula

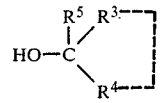

wherein $R^3$ is a hydrogen atom or an optionally substituted hydrocarbyl or heterocyclic group; $R^4$ is a hydrogen atom, an optionally substituted hydrocarbyl group; or $R^3$ and $R^4$, when taken together with the carbon atom to which they are attached, form an alkylene group as denoted by the dotted line; and $R^5$ is a hydrogen atom, an optionally substituted hydrocarbyl group or a group $-C(=X^1)X^1)R^6$ in which each $X^1$ is independently O or S and $R^6$ is an optionally substituted hydrocarbyl group.

5. A process according to claim 3 which is conducted in the presence of a non-hydroxylic solvent.

6. A process according to claim 5 wherein the catalyst is histidine or a histidine-containing di- or polypeptide in which at least one of the histidyl-free N-H and free COOH groups is modified with a protecting group into the form of an amide, or an acid addition salt thereof, and ester group respectively; or the reaction product of one mole of a histidine or histidine-containing di- or polypeptide with about one mole of a ketene.

7. A process according to claim 6 wherein the di- or polypeptide also contains an alanine.

8. A process according to claim 6 wherein the histidine moiety in the catalyst is histidine, 3-methyl-histidine, 3-ethylhistidine, 3-propylhistidine, 3-benzylhistidine, 1-methylhistidine, 1-ethylhistidine, 1-propylhistidine or 1-benzylhistidine.

9. A process according to claim 7 wherein the catalyst is a cyclic dipeptide containing a histidine moiety and an alanine moiety.

10. A process according to claim 3 wherein the catalyst is optically active and selected from histidine, alpha-methyl-histidine, 1-methyl-histidine, 3-methylhistidine, cyclo(histidyl-histidine), (benzyloxycarbonylalanyl)-histidine methyl ester, cyclo(alanyl-histidine), cyclo(phenylalanyl-histidine), cyclo(beta-phenylalanyl-1-methylhistidine), cyclo(beta-phenylalanyl-3-methylhistidine), histidine methyl ester hydrochloride, histidine ethyl ester dihydrochloride, anserine, cyclo(valyl-histidine), glycyl-histidine, cyclo(-phenylalanylglycyl-histidine), cyclo(leucyl-histidine), cyclo(homophenylalanylhistidine), cyclo(phenylalanyl-methylhistidine), N-alpha-(beta-naphthoyl)histidine, histidyl-alanine, histidyl-phenylalaninamide hydrochloride, histidyl-phenylalanine, cyclo(histidyl-proline) or cyclo(glycyl-histidine) in free or protected form or a reaction product thereof with a ketene.

11. A process according to claim 6 wherein the catalyst is present in an amount of about 0.01 to about 5 mole percent based upon the weight of the alcohol.

12. A process according to claim 11 wherein the catalyst is present in an amount of about 0.1 to about 2.5 mole percent based upon the weight of the alcohol.

13. A process according to claim 1 wherein the alcohol is an optically-active, aromatic, alpha-substituted alcohol containing an optionally-substituted phenyl, naphthyl or 2-furanyl ring.

14. A process according to claim 13 wherein the alpha-substitution is a methyl, cyclohexyl, vinyl, propenyl, ethynyl, phenylethynyl, trifluoromethyl, allenyl or phenyl group.

15. A process according to claim 6 wherein the alcohol has the formula

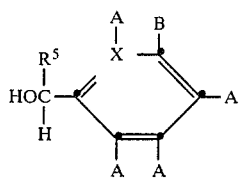

wherein each A is independently a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; B is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive, or is a group

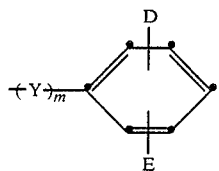

in which Y is O, $CH_2$; or C(O); m is 0 or 1 and D and E each independently is a hydrogen atom, a halogen atom having an atomic number of from 9 to 35, inclusive, or an alkyl, alkenyl or alkoxy group containing 1 to 6 carbon atoms, each optionally substituted by one or more halogen atoms having an atomic number of from 9 to 35, inclusive; and $R^5$ is a hydrogen atom or an alkyl, alkenyl, alkynyl, aralkyl or aryl group containing up to 8 carbon atoms.

16. A process according to claim 1 wherein the non-symmetrical ketene has the formula

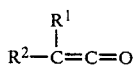

wherein $R^1$ is isopropyl or cyclopropyl optionally substituted by one or more chlorine atoms; $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 to 4 carbon atoms.

17. A process according to claim 16 wherein in the ketene $R^1$ is isopropyl and $R^2$ is a phenyl group para-substituted by halogen, alkyl, haloalkoxy in which the halogen is chlorine or fluorine and the alkyl contains 1 to 4 carbon atoms.

18. A process according to claim 17 wherein the ketene is (4-chlorophenyl)isopropylketene, (4-(difluoromethoxy)phenyl)isopropylketene, or (4-(trifluoromethyl)-3-(chlorophenyl)benzyloxycarbonylamino)isopropylketene.

19. A process according to claim 1 wherein the ketene is prepared by treating the corresponding acid halide with a tertiary amine.

20. A process according to claim 19 wherein the acid halide is isopropyl-(4-chlorophenyl)acetyl chloride.

21. A process for the preparation of an alpha-chiral carboxylic acid which comprises reacting a non-symmetrical ketene with an optically-active or achiral alcohol in the presence of an optically-active nitrogen-base-substituted amino acid, a di- or polypeptide thereof or the reaction product of about one mole to about three moles of a ketene with one mole of the nitrogen-base-substituted amino acid or di- or polypeptide thereof, followed by separation of the resulting ester diastereoisomers and hydrolysis of the resulting ester diastereoisomer to give the desired acid.

22. A process according to claim 21 wherein the catalyst is histidine or a histidine-containing di- or polypeptide in which at least one of the histidyl-free N-H and free COOH groups is modified with a protecting group into the form of an amide, or an acid addition salt thereof, and ester group respectively; or the reaction product of one mole of a histidine or histidine-containing di- or polypeptide with about one mole of a ketene.

23. A process according to claim 21 wherein the optically-active alcohol is an aromatic alpha-substituted alcohol containing an optionally-substituted phenyl, naphthyl or 2-furanyl ring.

24. A process according to claim 21 wherein the non-symmetrical ketene has the formula

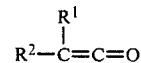

wherein $R^1$ is isopropyl or cyclopropyl optionally substituted by one or more chlorine atoms and $R^2$ is an alkyl group containing 1 to 6 carbon atoms; an alkenyl group containing 2 to 6 carbon atoms; a naphthyl group, a phenyl group or a (benzyloxycarbonyl)phenylamino group each optionally ring substituted by one or more of halogen, alkyl, haloalkyl, alkoxy, haloalkoxy in which the halogens are bromine, chlorine or fluorine and the alkyl or cycloalkyl group contains 1 or 4 carbon atoms.

25. A process according to claim 24 wherein in the ketene $R^1$ is isopropyl and $R^2$ is a phenyl group para-substituted by halogen, alkyl, haloalkoxy in which the halogen is chlorine or fluorine and the alkyl contains 1 to 4 carbon atoms.

26. A process according to claim 21 wherein the non-symmetrical ketene is prepared by treating the corresponding acid halide with a tertiary amine.

* * * * *